US 10,813,574 B2

(12) United States Patent
Fleig et al.

(10) Patent No.: US 10,813,574 B2
(45) Date of Patent: Oct. 27, 2020

(54) DETERMINING A RANGE OF MOTION OF AN ARTIFICIAL KNEE JOINT

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventors: Oliver Fleig, Baldham (DE); Christian Brack, Neusaess (DE); Zohar Leder, Munich (DE); Martin Bauer, Munich (DE)

(73) Assignees: Smith & Nephew, Inc., Memphis, TN (US); Smith & Nephew Asia Pacific Pte. Limited, Singapore (SG); Smith & Nephew Orthopaedics AG, Zug (CH)

( * ) Notice: Subject to any disclaimer, the term of this patent is extended or adjusted under 35 U.S.C. 154(b) by 443 days.

(21) Appl. No.: 15/794,754

(22) Filed: Oct. 26, 2017

(65) Prior Publication Data
US 2018/0140232 A1    May 24, 2018

Related U.S. Application Data

(63) Continuation of application No. 14/405,427, filed as application No. PCT/EP2012/061188 on Jun. 13, 2012, now abandoned.

(51) Int. Cl.
*A61B 5/11* (2006.01)
*A61B 34/20* (2016.01)
(Continued)

(52) U.S. Cl.
CPC .......... *A61B 5/1121* (2013.01); *A61B 5/1072* (2013.01); *A61B 5/4585* (2013.01);
(Continued)

(58) Field of Classification Search
CPC ... A61B 5/1121; A61B 19/5212; A61B 19/54; A61B 19/50; A61B 19/547;
(Continued)

(56) References Cited

U.S. PATENT DOCUMENTS

2004/0254771 A1   12/2004  Riener
2005/0251148 A1*  11/2005  Friedrich ............... A61B 90/36
                                                                606/88
(Continued)

FOREIGN PATENT DOCUMENTS

DE       102006056399        5/2007

OTHER PUBLICATIONS

Walde et al. "Optimized Functional Femoral Rotation in navigated Total knee Arthroplasty Considering Ligament Tension", The Knee, vol. 17, No. 6, Dec. 1, 2010, pp. 381-386.
(Continued)

*Primary Examiner* — Angela M Hoffa
*Assistant Examiner* — Helene Bor
(74) *Attorney, Agent, or Firm* — Troutman Pepper Hamilton Sanders LLP

(57) ABSTRACT

A data processing method for determining a range of motion of an artificial knee joint which connects a femur and a tibia via a medial ligament and a lateral ligament, wherein at least the femur comprises an implant which forms a medial condyle and a lateral condyle, the method comprising the steps of: acquiring the maximum lengths of the lateral ligament and the medial ligament for a particular flexion angle of the knee joint; calculating a first virtual position between the femur and the tibia in which the lateral condyle of the femoral implant touches the tibia and the medial ligament is stretched to its maximum length; calculating a maximum valgus angle of the range of motion from the first virtual position; calculating a second virtual position
(Continued)

Figure 1:
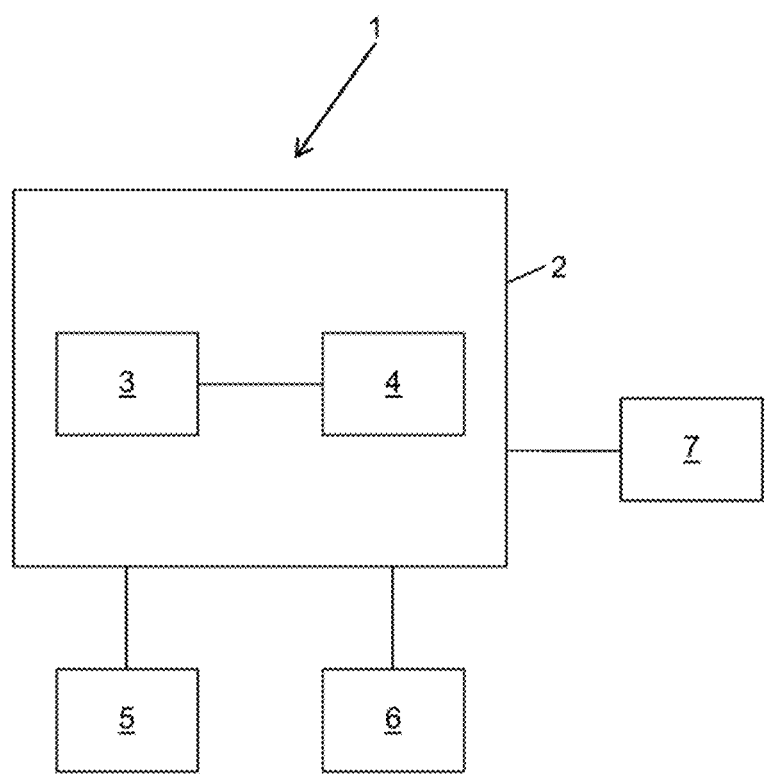

between the femur and the tibia in which the medial condyle of the femoral implant touches the tibia and the lateral ligament is stretched to its maximum length; and calculating a maximum varus angle of the range of motion from the second virtual position.

18 Claims, 12 Drawing Sheets

(51) Int. Cl.
*A61B 90/00* (2016.01)
*A61B 34/10* (2016.01)
*A61B 5/107* (2006.01)
*A61B 5/00* (2006.01)

(52) U.S. Cl.
CPC .............. *A61B 34/10* (2016.02); *A61B 34/20* (2016.02); *A61B 90/361* (2016.02); *A61B 90/39* (2016.02); *A61B 2034/104* (2016.02); *A61B 2034/2055* (2016.02); *A61B 2090/397* (2016.02)

(58) Field of Classification Search
CPC . A61B 17/154; A61B 19/5244; A61B 5/4533; A61B 5/4528; A61B 2019/502; A61B 2019/505; A61B 34/10; A61B 2090/397; A61B 34/20; A61B 90/361; A61B 90/39; A61B 5/1072; A61B 5/4585; A61B 2034/104; A61B 2034/2055; A61F 2/3859
See application file for complete search history.

(56) References Cited

U.S. PATENT DOCUMENTS

| | | |
|---|---|---|
| 2006/0161051 A1 | 7/2006 | Terrill-Grisoni |
| 2007/0179626 A1 | 8/2007 | de la Barrera et al. |
| 2008/0243127 A1 | 10/2008 | Lang |
| 2008/0262812 A1* | 10/2008 | Arata ................. A61F 2/3859 703/11 |
| 2010/0049195 A1 | 2/2010 | Park |
| 2014/0324403 A1* | 10/2014 | Gotte ................. A61B 90/37 703/2 |

OTHER PUBLICATIONS

International Search Report and Written Opinion for International Application No. PCT/EP2012/061188 dated Mar. 11, 2013.
Van der Esch, et al., "Knee Varus-Valgus Motion During Gait—a Measure of Joint Stability in Patients with Osteoartritis?" Osteoarthritis and Cartilage, Vo. 16, No. 4, Mar. 29, 2008, pp. 522-525.

* cited by examiner

DETERMINING A RANGE OF MOTION OF AN ARTIFICIAL KNEE JOINT

The present invention relates to a data processing method, a computer program, a computer and a medical navigation system for determining a range of motion of an artificial knee joint.

A knee joint connects a femur and a tibia. One characteristic for describing the knee joint is its range of motion. In this document, "range of motion" means the range between the maximum varus angle and the maximum valgus angle for a particular flexion angle between the femur and the tibia. In other words, the range of motion describes the maximum tilt between the femur and the tibia in the coronal plane. The range of motion can optionally be given for a plurality of flexion angles, thus resulting in an envelope which describes the maximum varus/valgus angle over the range of flexion angles.

The range of motion is of particular interest in the case of an artificial knee joint, where the range of motion refers to the post-operative range of motion. In an artificial knee joint, at least the femur comprises an implant at its distal end. The implant forms a medial and a lateral condyle, thus recreating the original bone. Typically, the proximal end of the tibia is cut off. This cut is defined by a cutting plane. A tibial implant is typically, though not necessarily, placed onto the tibial cut.

Where a "bone" is mentioned in this document, this may refer to the bone itself or any implant attached (or to be attached) to the bone. The expression "femur" therefore relates to the femur alone or to a combination of the femur and a femoral implant, and the expression "tibia" may refer to the tibia alone or to a combination of the tibia and a tibial implant.

The aim of a total knee arthroplasty is to achieve a proper functionality of the artificial knee joint. This is assessed on the basis of the post-operative range of motion. It is therefore an object of the present invention to determine the range of motion before the arthroplasty is actually performed. "Determining" thus has the meaning here of "simulating" or "predicting". From this (predicted) post-operative range of motion, it is possible to determine whether or not the parameters, such as the selected implant(s) or the position or positions, are correct and will lead to a desired result.

The present invention relates to a method for determining a range of motion of an artificial knee joint which connects a femur and a tibia via a medial ligament and a lateral ligament, wherein at least the femur comprises an implant which forms a medial condyle and a lateral condyle. The method comprises the step of acquiring the maximum lengths of the lateral ligament and the medial ligament for a particular flexion angle of the knee joint. The maximum length of a ligament is the maximum length to which the ligament can be stretched, in particular without causing damage to the ligament.

The method also comprises the step of calculating a first virtual position between the femur and the tibia in which the lateral condyle of the femoral implant touches the tibia and the medial ligament is stretched to its full length. This first virtual position depends on the structure of the femoral implant, the position of the femoral implant on the femur, the maximum length of the medial ligament and the shape of the tibia (including, where applicable, a tibial implant). The next step then relates to calculating a maximum valgus angle of the range of motion from the first virtual position.

The method also comprises the step of calculating a second virtual position between the femur and the tibia in which the medial condyle of the femoral implant touches the tibia and the lateral ligament is stretched to its maximum length and the step of calculating a maximum varus angle of the range of motion from the second virtual position. These two steps are analogous to the steps of calculating the first virtual position and the maximum valgus angle, but relate to the knee joint being bent outwards rather than inwards.

Preferably, the internal external rotation, the anterior/posterior location and the lateral location are identical fir the first and second virtual positions. The flexion angle is necessarily identical for the first and second virtual positions. Within this document, the term "position" means the spatial location in up to three translational dimensions and/or the rotational alignment in up to three rotational dimensions.

Given the maximum varus and valgus angles, the range of motion of the artificial knee joint for the particular flexion angle is known. The process of determining the range of motion, or at least one of the maximum varus angle and maximum valgus angle, of the artificial knee joint can he repeated for a plurality of flexion angles in order to obtain an envelope of the range of motion over a range of flexion angles.

Within the scope of the present invention, the acquiring step does not involve manipulating a body in any way but rather merely receiving data, in particular maximum length datasets which represent the maximum length of the lateral ligament and the medial ligament. The present invention can however also comprise non-surgical procedures for measuring the maximum length.

The expression "acquiring data" encompasses in particular the scenario (within the framework of a data processing; method) in which the data are determined by the data processing method or program. Determining data in particular encompasses measuring physical quantities and transforming the measured values into data, in particular digital data, and/or computing the data by means of a computer, in particular by computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.), or via the interface (for instance, from another computer or a network). The data can be made "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably referred to as "XY information".

Within the anatomy of a knee joint, a ligament connects to the femur at a defined point and to the tibia at a defined point. Due to the shape of the bones, in particular the tibia, a ligament might not be straight. It can therefore be advantageous to not consider the actual length of the ligament, but to instead define the length of a ligament as the distance between the point on the femur at which the ligament connects to the femur and a plane defined with respect to the tibia. This plane which is defined with respect to the tibia is preferably the tibial cutting plane. This tibial cutting plane is either a planned (virtual) cutting plane or the plane of a cut which has been performed before the method according to the present invention is carried out and which does not form part of the present invention. A tibial cutting plane is typically, though not necessarily, perpendicular to the mechanical axis of the tibia and therefore a transverse plane.

In one embodiment of the invention, calculating a virtual position includes the step of calculating a virtual contact position in which both the lateral condyle and the medial condyle of the femur touch the tibia and the step of rotating the femur about the contact point between one of the condyles and the tibia until the opposing ligament is stretched to its maximum length. The opposing ligament with respect to the lateral condyle is the medial ligament and the opposing ligament with respect to the medial condyle is the lateral ligament. This approach starts from a stable virtual contact position in which both condyles are in contact with the tibia without penetrating into the tibia. The femur is then rotated about one of the contact points as far as the opposing ligament permits, thus resulting in the maximum possible varus or valgus angle.

In one embodiment, calculating the virtual contact position comprises the step of rotating the femur until its condyles have the same distance from the tibia (or, preferably, from the tibial cutting plane) and the step of moving the femur translationally relative to the tibia until both the condyles of the femur touch the tibia, i.e. the femur and the tibia are first aligned and then brought into contact.

As outlined above, the maximum length of a ligament is determined from a relative position between the femur and the tibia in which the ligament is stretched to its maximum length. Since the feature point on the femur at which the ligament connects is known, the position of this point, in particular relative to the tibia, is also known or can be determined. In another embodiment of the invention, a (first or second) virtual position is calculated by rotating the femur about said point until the condyle opposite the stretched ligament touches the tibia. This approach is complementary to the previously described approach in which a contact point is first determined and a rotation is then performed until a ligament is fully stretched.

In one embodiment of the present invention, a surface model of the femur and preferably also of the tibia is used for the calculating steps. The calculating steps comprise calculating a virtual position or a virtual contact position. A surface model of a bone represents the three-dimensional structure of the surface of the bone, for example as a grid model or a three-dimensional image dataset. Within this approach, collision techniques can be used in order to determine whether or not the femur and the tibia are in contact. A surface model of the tibia (or the tibial implant) or a plane defined in relation to the tibia can be used in the calculating steps.

As an alternative to using a surface model of the femur, the femur can also be described mathematically. The condyles of the femur in particular can be described mathematically because they are in contact with the tibia. The condyles of the femur are preferably modelled by a mathematical function and preferably as ellipses. Within this approach, geometrical methods can be used to calculate the contact position in which at least one condyle of the femur touches the tibia.

Not only the pivotal point but also an axis of rotation is required in order to define a rotation. Preferably, the axis of rotation is parallel to a cutting plane of the tibia (either a planned cutting plane or an actual cutting plane) and lies within the sagittal plane of the tibia. The axis of rotation is also deemed to be parallel to the cutting plane if the axis of rotation lies within the cutting plane. With such an axis of rotation, the rotation does not change the internal/external angle or the flexion angle.

In one embodiment, the maximum length of a ligament is calculated from a transformation matrix which represents a relative position between the femur and the tibia in which the ligament is stretched to its maximum length. This transformation matrix represents all the degrees of freedom (up to three rotational and/or up to three translational degrees of freedom) of the relative position and is for example a homogeneous 4×4 matrix. Homogeneous matrices are used to unify the calculations of three-dimensional rotations and translations in a four-dimensional space. This matrix can be determined by observing marker devices which are attached to at least one of the bones, preferably with one marker device attached to each bone, wherein a bone is registered to the marker device attached to it. It should be noted that the process of attaching a marker device to a bone or of registering a bone to a marker device, for example using a pointer, is not part of the present invention, but is performed before the range of motion is determined.

It is the function of a marker to be detected by a marker detection device (for example, a camera or an ultrasound receiver or analytical devices such as CTs or MRIs), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or a pointer or one marker or a plurality of (individual) markers which are preferably in a predetermined spatial relationship. A marker device comprises one, two, three or more markers, wherein if there are two or more markers, these are in a predetermined spatial relationship. This predetermined spatial relationship is in particular known to a navigation system and for example stored in a computer of the navigation system.

Merely for informational purposes, two possible approaches for ensuring that a ligament is stretched to its maximum length are described here. In the first approach, a varus or valgus stress is applied to the knee joint, for example by exerting an external lateral force on the knee, such that the ligament is fully stretched. This is performed once with a varus stress for acquiring a transformation matrix which represents a fully stretched lateral ligament and once with a valgus stress for acquiring a transformation matrix Which represents a fully stretched medial ligament. If the range of motion is to be determined for a plurality of flexion angles, it is preferable to sample a plurality of transformation matrices by applying a lateral (varus or valgus) stress to the knee joint and bending the knee over a range of flexion angles while taking the transformation matrix samples.

In a second approach, a spreading device is inserted into the knee joint and adjusted such that both ligaments are fully stretched. In this case, a single transformation matrix is sufficient to calculate the maximum length of both the medial and the lateral ligament. As in the first approach, the knee can be bent over a range of flexion angles in order to determine a plurality of transformation matrix samples and so obtain an envelope of the range of motion.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can he a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The method in accordance with the invention is in particular a data processing method. The data processing method is preferably performed using technical means, in particular a computer. The data processing method is in particular executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the Internet (world wide web). In particular, the cloud provides computing infrastructure as a service. The cloud computer can function as a virtual host for an operating system and/or data processing application which is used to execute the method of the invention. The cloud computer is for example an elastic compute cloud (EC2) such as is provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The present invention also relates to a medical navigation system comprising a computer as described above and at least one of a stereoscopic camera and an electromagnetic receiver. The stereoscopic camera or the electromagnetic receiver is used to ascertain the position of a marker device attached to a bone. A stereoscopic camera captures a three-dimensional image from which the position of the marker relative to the camera can be calculated. An electromagnetic receiver receives electromagnetic radiation emitted from a marker device attached to a bone. The position of the marker device relative to the electromagnetic receiver can be calculated from the received electromagnetic signal.

It is within the scope of the present invention to combine one or more features of two or more embodiments, where technically feasible, to form another embodiment. It is also within the scope of the present invention to omit features which are not essential to implementing the inventive concept or to replace such a feature with another feature, in particular a feature exhibiting a similar function.

Figure 2:
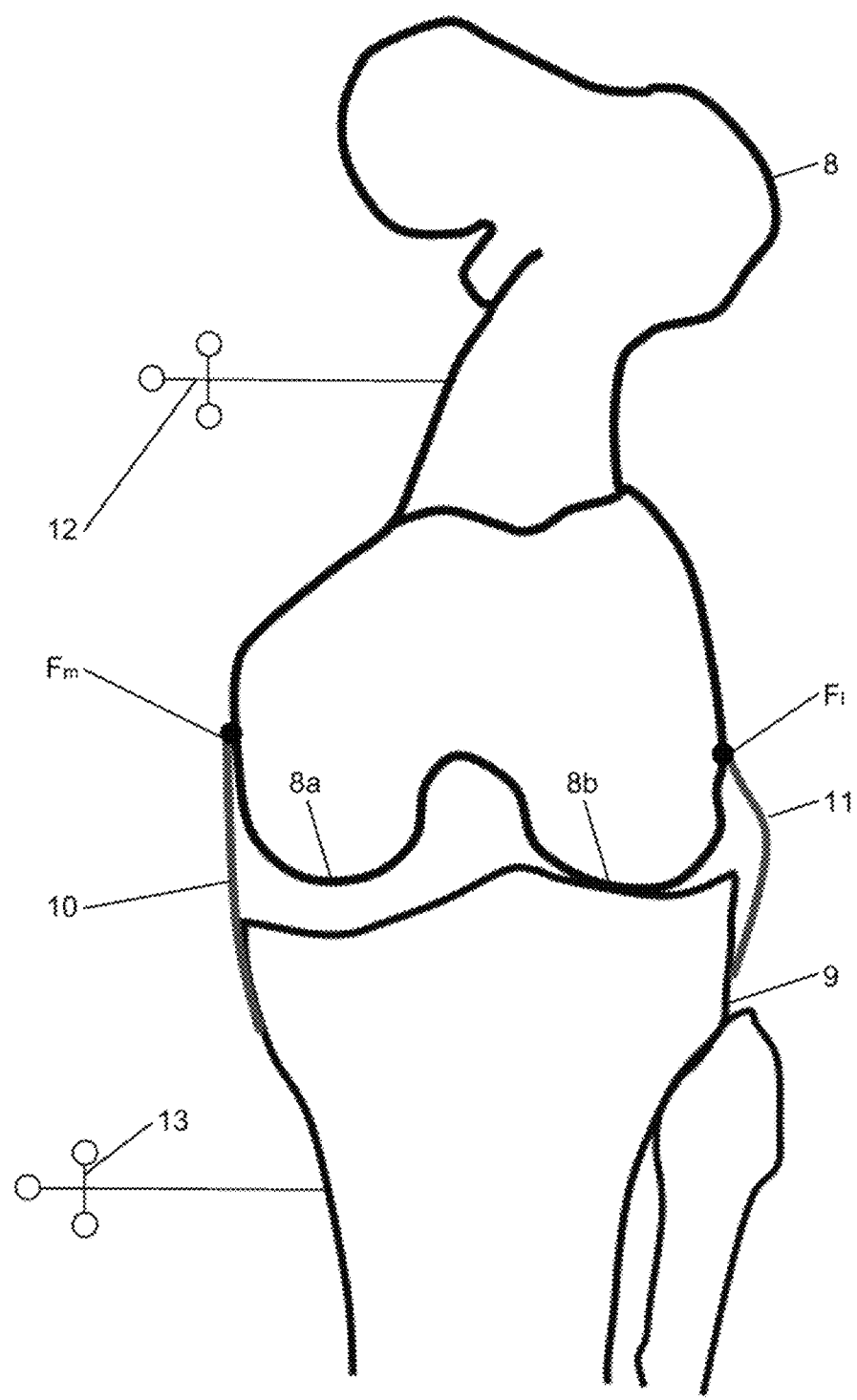
Figure 3:
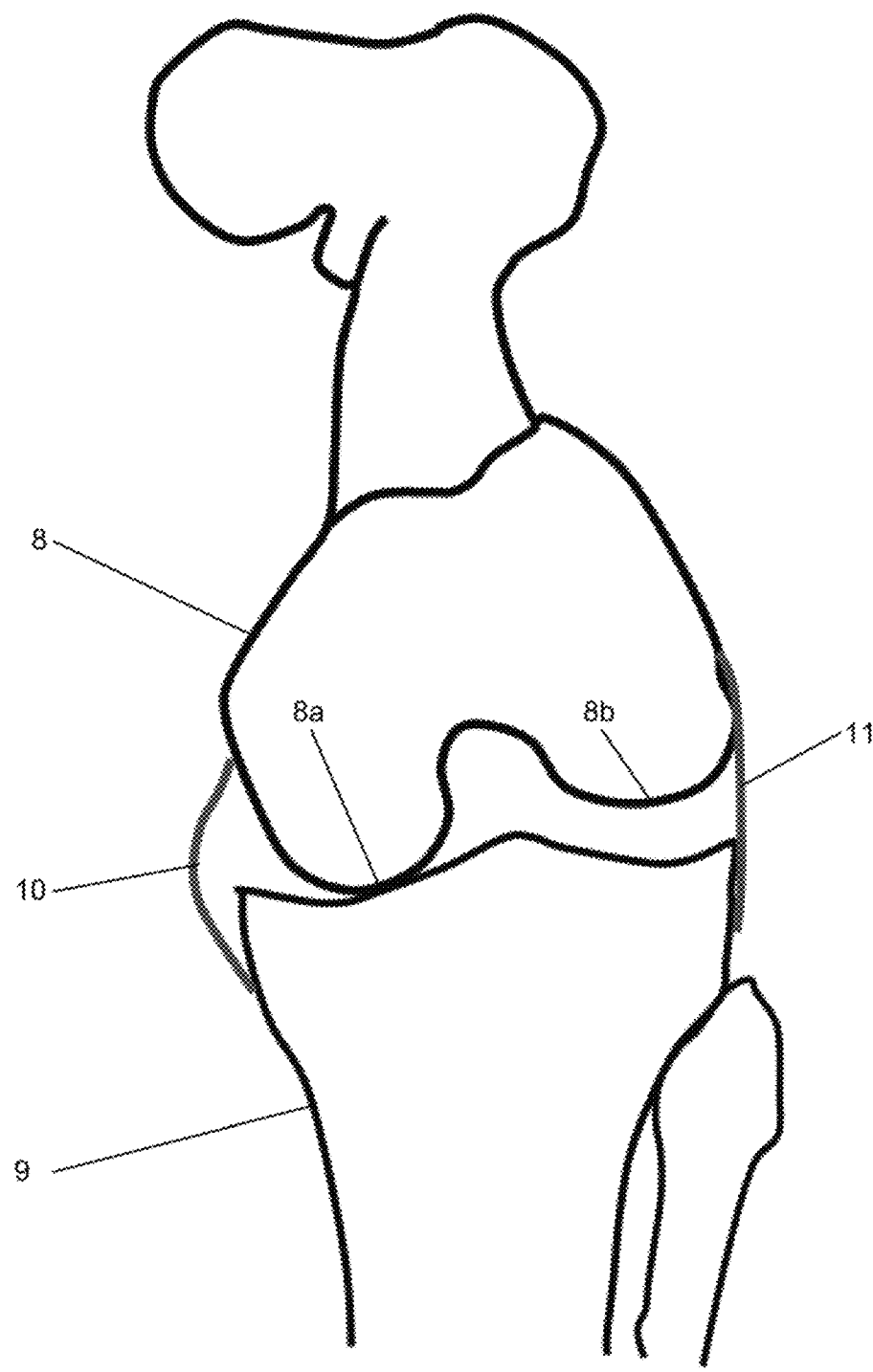
Figure 4:
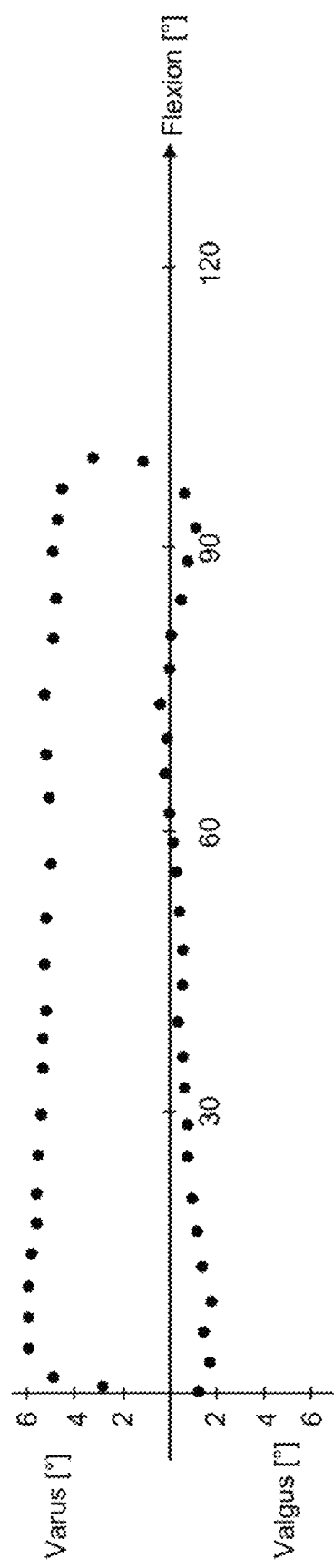
Figure 5B:
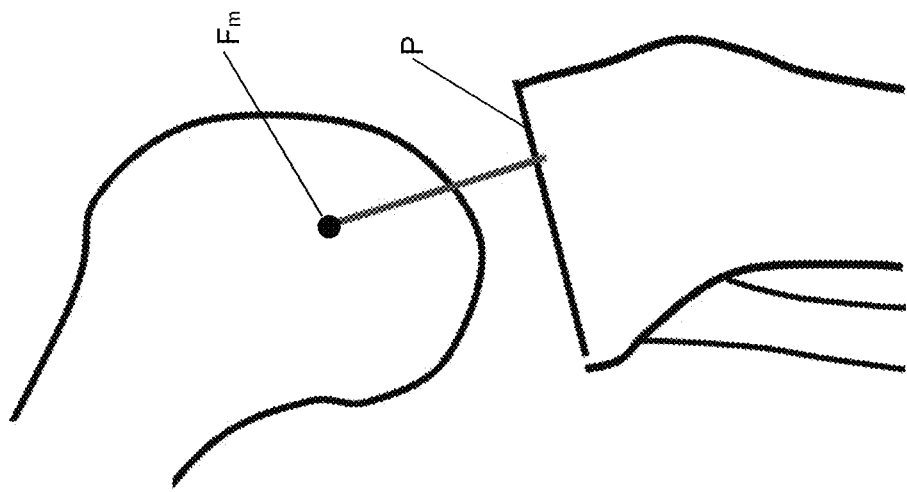
Figure 5A:
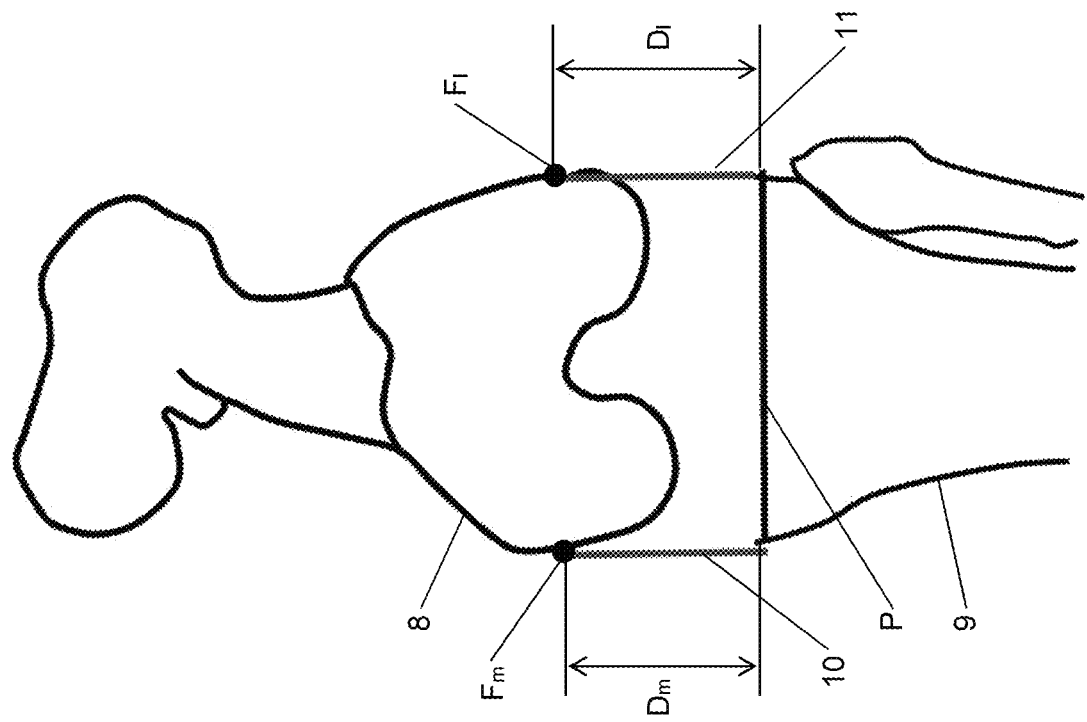
Figure 6:
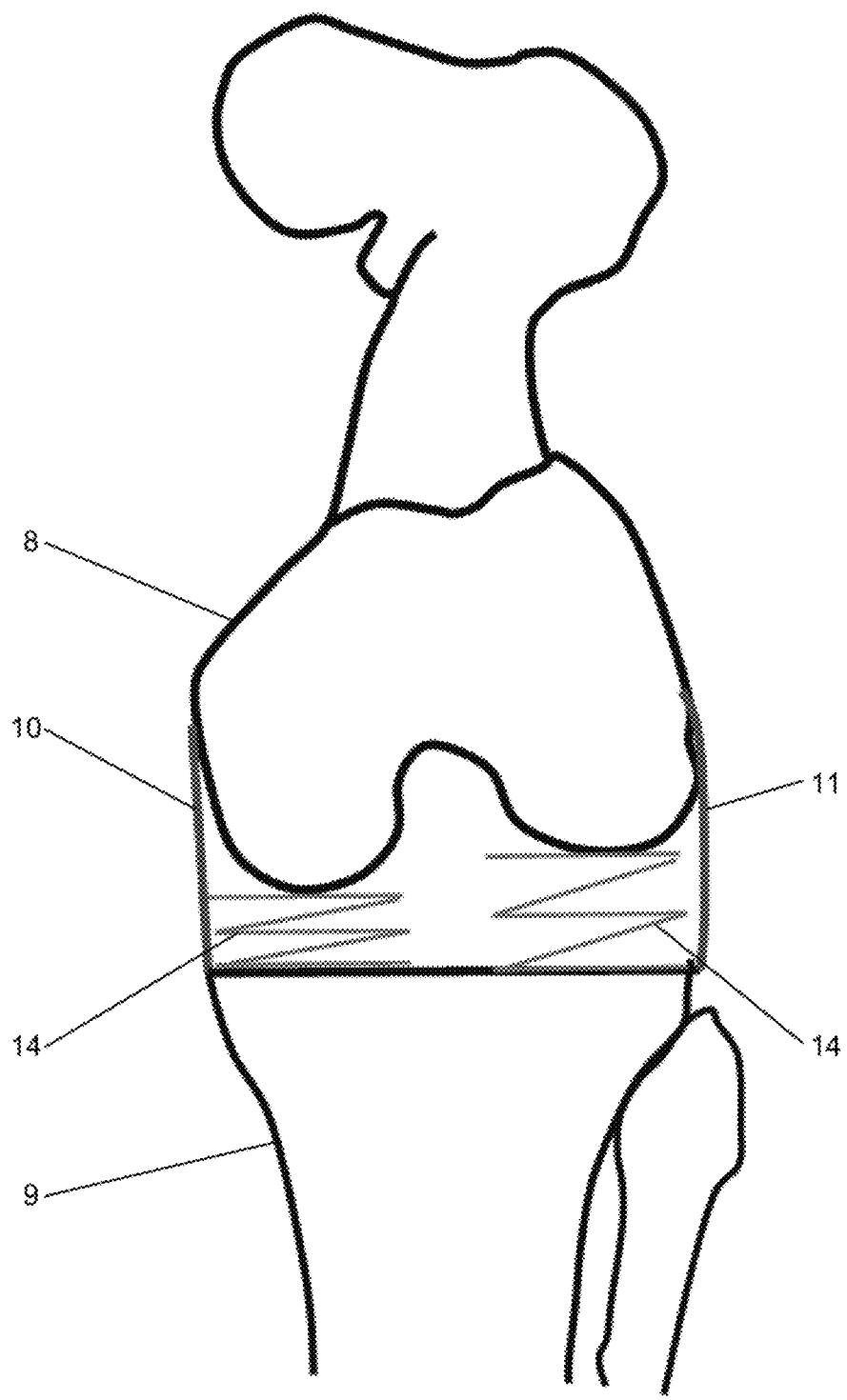
Figure 7:
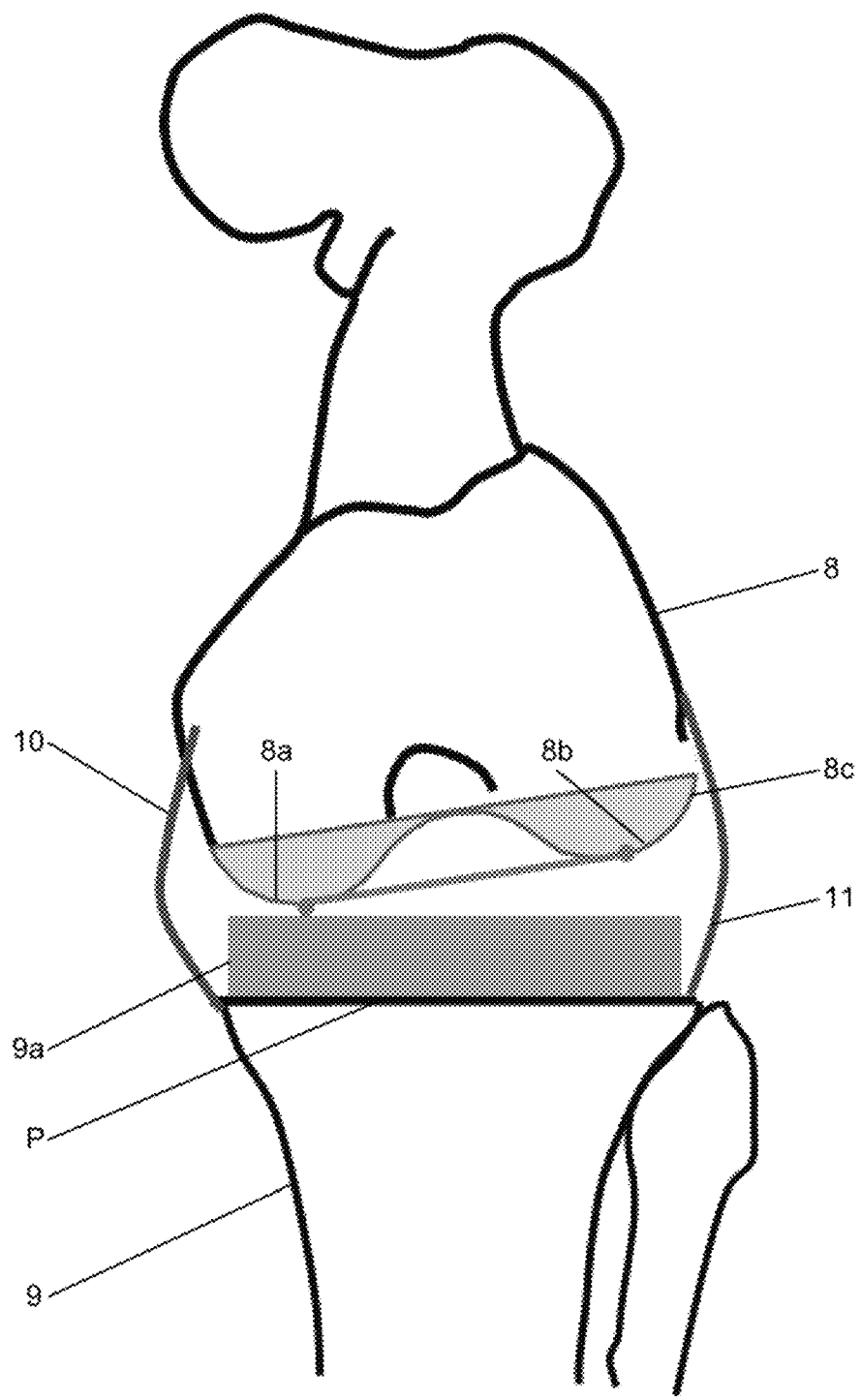
Figure 8:
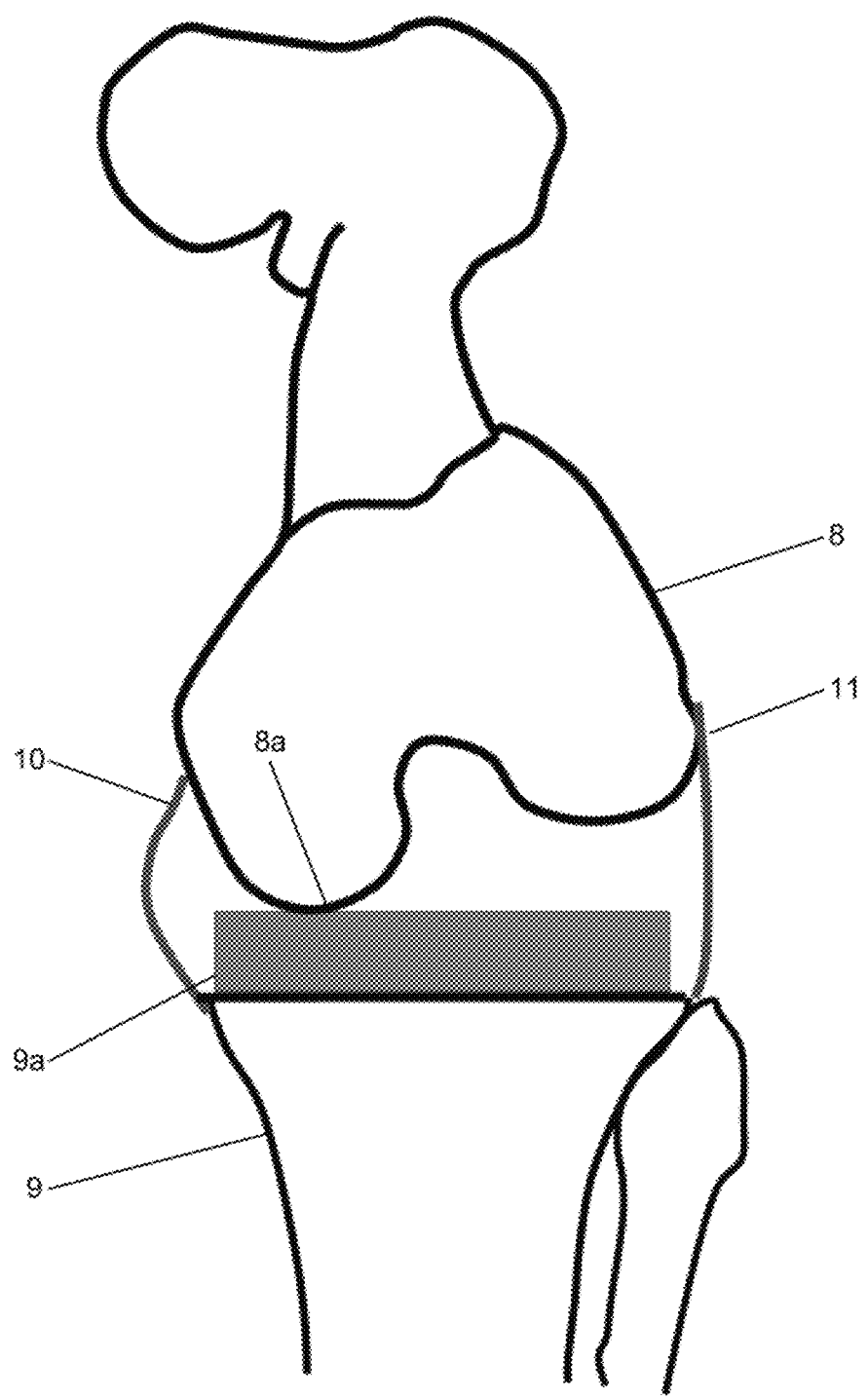
Figure 9:
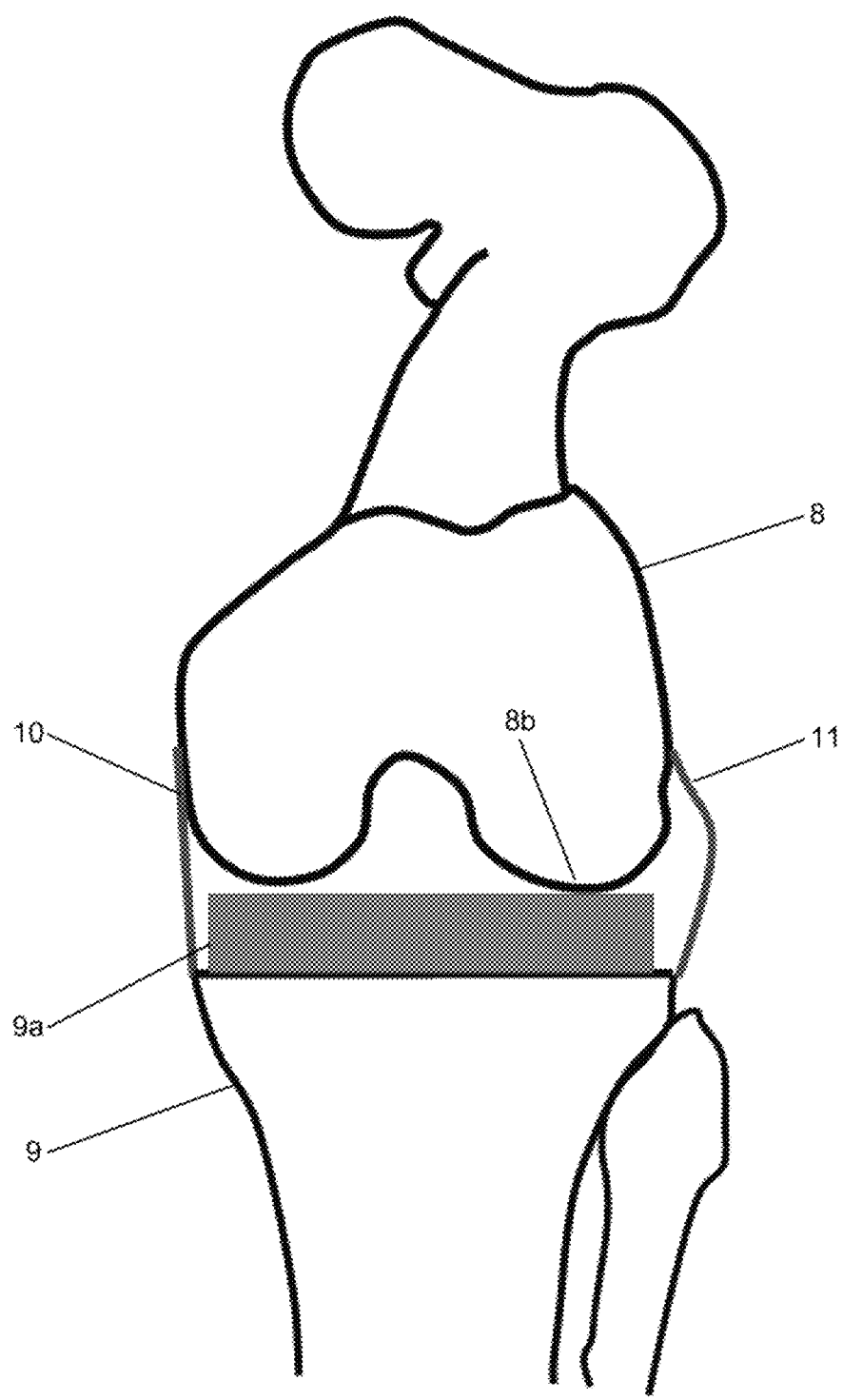
Figure 10:
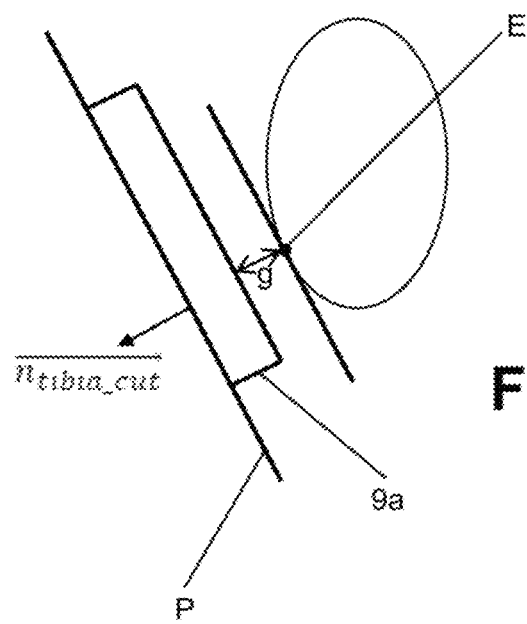
Figure 11:
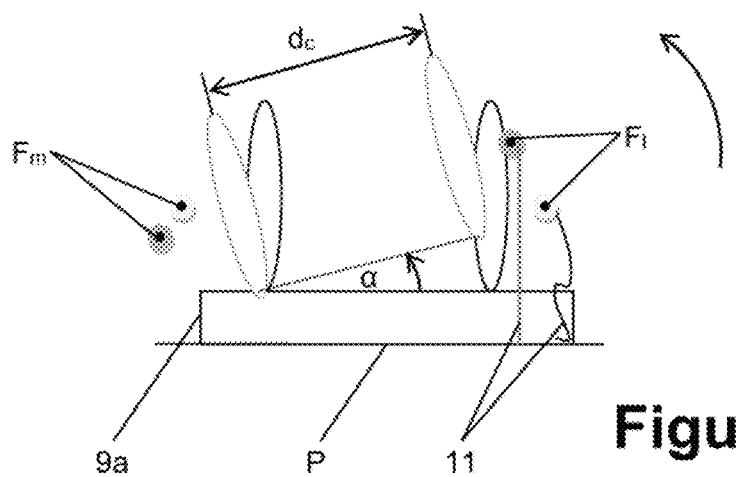
Figure 12:
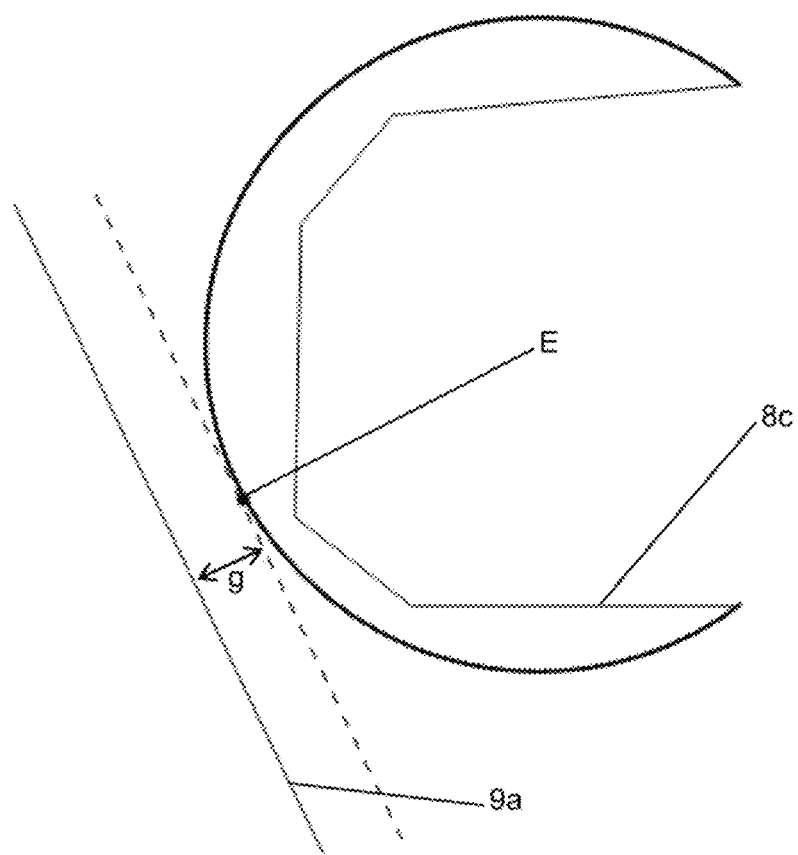

The invention shall now be explained in more detail with reference to the accompanying figures, which show:

FIG. 1 a medical navigation system for carrying out the invention;

FIG. 2 a pre-operative knee joint, with the medial ligament stretched;

FIG. 3 the knee joint of FIG. 2, with the lateral ligament stretched;

FIG. 4 an envelope of the pre-operative range of motion;

FIG. 5A a frontal view of a knee joint for explaining a ligament model;

FIG. 5B a side view of a knee joint of FIG. 5A;

FIG. 6 the knee joint of FIG. 1 after a tibial cut, together with a spreading device;

FIG. 7 a knee joint comprising a femoral and a tibial implant;

FIG. 8 the knee joint of FIG. 7 with a varus stress applied to it;

FIG. 9 the knee joint of FIG. 7 with a valgus stress applied to it;

FIG. 10 an ellipse which is used as a model for the femoral implant;

FIG. 11 a model for calculating the maximum varus angle;

FIG. 12 a surface model of a femoral implant; and

Figure 13:
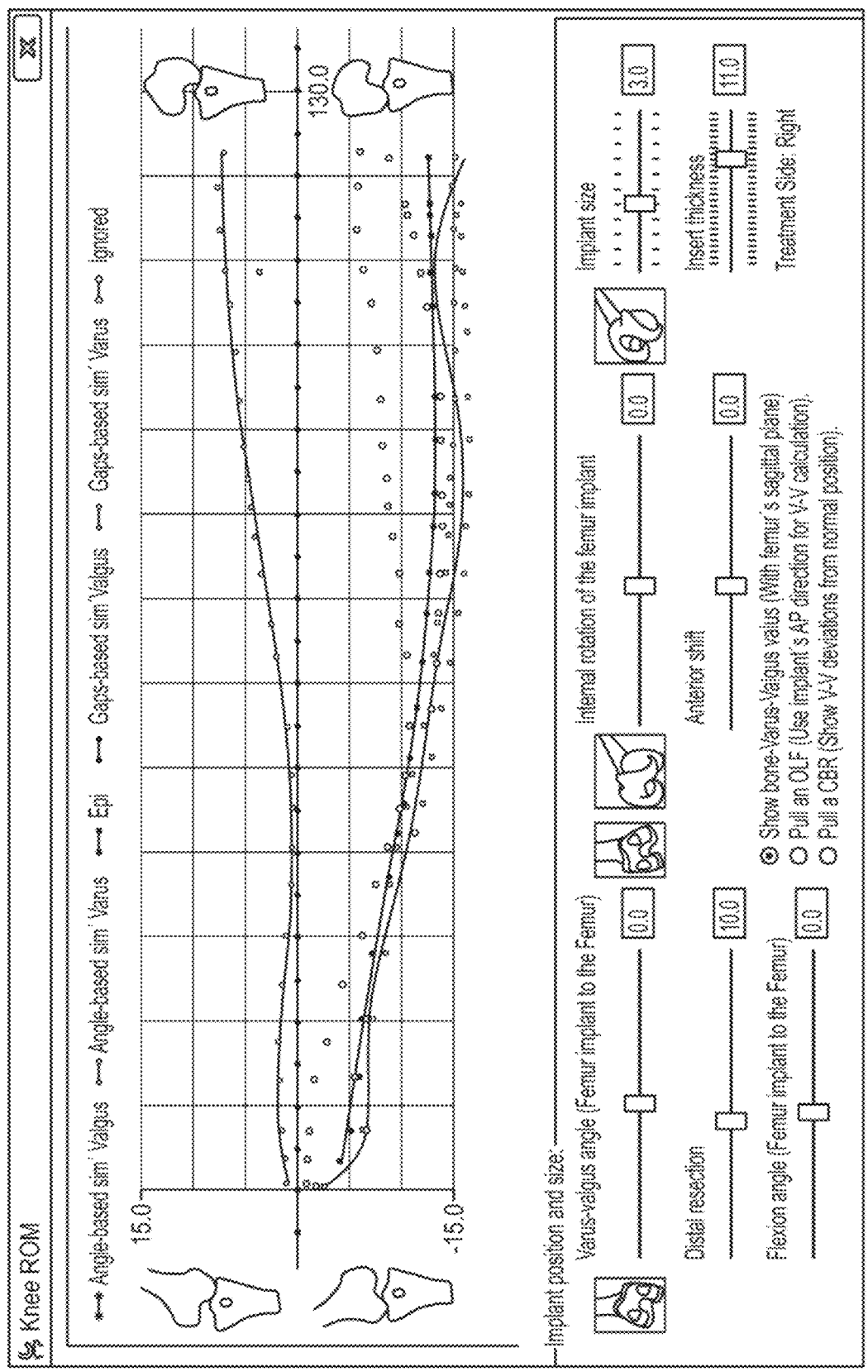

FIG. 13 a screenshot showing a calculated envelope of the range of motion.

FIG. 1 shows the basic structure of a medical navigation system 1. The medical navigation system 1 comprises a computer 2 which is connected to a display device 5, to an input device 6 and to a stereoscopic camera 7. The display device 5 is configured to display information acquired or calculated by the computer 2. The input device 6, such as a keyboard, a mouse, a trackball, a touch screen or a combination of these, is configured to receive information and provide data corresponding to the information to the computer 2. The computer 2 comprises a central processing unit (CPU) 3 and a memory 4. The CPU 3 performs the method of the present invention by processing data. The memory 4 comprises data to be processed by the central processing unit 3 and/or program code to be executed by the CPU 3. The stereoscopic camera 7 captures a three-dimensional image from which the position of a marker device, and therefore the position of an object to which the marker device is attached, can be calculated. This calculation can be performed in the camera 7, in the CPU 3 or by both in combination.

FIG. 2 shows a pre-operative knee joint between a femur 8 and a tibia 9.

The femur 8 comprises a medial condyle 8a and a lateral condyle 8b. When the knee joint is bent, the femoral condyles 8a and 8b roll and/or glide on the corresponding surface of the tibia 9. The femur 8 and the tibia 9 are connected by a medial ligament 10 which connects to a feature point $F_m$ of the femur 8, namely the medial epicondyle. A lateral ligament 11 which connects the femur 8 and the tibia 9 is correspondingly connected to another feature point $F_l$ of the femur 8, namely the lateral epicondyle.

A marker device 12 is rigidly attached to the femur 8, and a marker device 13 is rigidly attached to the tibia 9. The femur 8 and tibia 9 are each registered with reference to the corresponding marker device 12 or 13, respectively, for example using a pointer (not shown). The registration data are stored in the memory 4 of the medical navigation system 1. Attaching a marker device to a bone or registering a bone to a marker device is not however part of the present invention.

In FIG. 2, the lateral condyle 8b of the femur 8 touches the surface of the tibia 9, while the medial ligament 10 is stretched to its maximum length. This relative position between the femur 8 and the tibia 9 represents a maximum valgus angle.

FIG. 3 shows the knee joint of FIG. 2, but with a varus stress applied to it. The medial condyle 8a of the femur 8 is in contact with the surface of the tibia 9, while the lateral ligament 11 is stretched to its maximum length. This relative position between the femur 8 and the tibia 9 represents the maximum varus angle. The difference between the maximum valgus angle and the maximum varus angle, with all other parameters such as internal/external rotation and flexion angle remaining unchanged, represents the range of motion of the knee joint.

The range of motion of the knee joint is preferably determined over a range of flexion angles. The envelope describing the range of motion over such a range of flexion angles can be interpolated from the maximum varus and/or valgus angles for the individual flexion angles sampled. For example, a varus stress is applied to the knee and the knee is bent over the range of flexion angles. Over this range, the medical navigation system samples the position of the marker devices 12 and 13 in order to calculate the relative position between these marker devices and therefore also between the femur 8 and the tibia 9. The maximum varus angle can be calculated for each sample, which corresponds to a particular flexion angle. A valgus stress is then correspondingly applied to the knee and the knee is bent over the range of flexion angles. A plurality of maximum valgus angles are calculated, which correspond to the plurality of flexion angles. The maximum varus and valgus angles over the range of flexion angles result in an envelope of the range of motion of the knee joint. An example of such an envelope is shown in FIG. 4. The horizontal axis represents the flexion angle, while the vertical axis represents the varus (upward) and valgus (downward) angle.

Due to the shape of the femur and the tibia, even a fully stretched ligament (a ligament stretched to its maximum length) is not completely straight but rather may comprise curved sections. In order to reduce computational complexity, the ligaments 10 and 11 are preferably considered to be straight. In addition, the maximum length of a ligament need not necessarily be defined as the maximum distance between the points at which the ligament is connected to the femur 8 and tibia 9, respectively. In this example embodiment, the length of a ligament is instead defined as the distance between the point $F_m$ or $F_l$ respectively, and a plane P which defines a tibial cut. The tibial cut can be an actual tibial cut which has been made prior to performing the present invention and which is therefore not part of the present invention, or a planned tibial cut. The ligaments 10 and 11 are considered to be perpendicular to the surface of the tibial cutting plane P. This is shown in FIGS. 5A and 5B which represent a frontal view and a side view of the knee joint, respectively.

In FIG. 5A, the maximum length of the medial ligament 10 is denoted as $D_m$ and the maximum length of the lateral ligament is denoted as $D_l$. Since the ligaments are connected to the femur and may twist for different flexion angles, the maximum length of a ligament may depend on the flexion angle. The maximum ligament lengths $D_m$ and $D_l$ are therefore also related to the index i, resulting in maximum ligament lengths $D_{m,i}$ and $D_{l,i}$.

In this process, a plurality of relative positions between the femur 8 and the tibia 9 are sampled, Each relative position is represented by a transformation matrix $T_i$, wherein 0<i<N is used as an index for identifying the individual samples within the plurality of samples and wherein the matrix is preferably a 4×4 matrix. Since the femur 8 and the tibia 9 are registered to their respective marker devices 12 and 13 the positions of the points $F_m$ and $F_l$ relative to the tibia 9 are also known or can be calculated.

FIG. 6 shows an alternative approach for determining the maximum ligament lengths $D_m$ and $D_l$. After the tibial cut has been performed, a spreading device 14 is inserted between the femur 8 and the tibia 9 and adjusted to fully stretch both the medial ligament 10 and the lateral ligament 11 at the same time. The maximum lengths can then be calculated from the relative position between the femur 8 and the tibia 9. This process can likewise be performed for a particular flexion angle or also over a range of flexion angles.

FIG. 7 shows a post-operative knee joint between the femur 8, which comprises a femoral implant 8c, and the tibia 9 which comprises a tibial implant 9a. The tibial implant 9a is also referred to as an insert or tray and can have the shape of a disc. The femoral implant 8c forms the medial condyle 8a and the lateral condyle 8b. In order to reduce computational complexity, the surface of the tibial implant 9a facing the femur 8 is considered to be planar. It should be noted that this post-operative knee joint is a virtual knee joint which is simulated before arthroplasty is actually completed.

The post-operative situation assumes a particular choice for the femoral implant 8c and tibial implant 9a and a particular position of the femoral implant 8c on the femur 8 and the tibial implant 9a on the tibia 9. The purpose of the present invention is to calculate the range of motion of the post-operative artificial knee joint if these assumptions were actually implemented. In view of the calculated range of motion, it is possible to amend one or more of these assumptions until a desired range of motion results.

For each sample, the distances $D_{m,i}$ and $D_{l,i}$ are calculated using the following equations:

$$d_{m,i}=|T_i \times F_{m,i}-P|$$

$$d_{l,i}=|T_i \times F_{l,i}-P|$$

The product of the transformation matrix $T_i$ and the position $F_{m,i}$ or $F_{l,i}$ of the feature points $F_m$ and $F_l$, respectively, transforms the corresponding point into the co-ordinate system of the tibia 9. The length of a ligament is then the shortest signed distance between this transformed point and the plane P of the tibial cut.

FIG. 8 shows a calculated relative position between the femur 8 and the tibia 9 for a virtual post-operative artificial knee joint in which the medial condyle 8a of the femur 8 (more specifically, the femoral implant 8c which is not explicitly designated in FIGS. 8 and 9) is in contact with the tibial implant 9a, and the lateral ligament 11 is stretched to its maximum length which has previously been calculated as $D_l$. This relative position represents the maximum varus angle for the given femoral and tibial implants and the particular flexion angle. FIG. 9 correspondingly shows a relative position between the femur 8 and the tibia 9 in which the lateral condyle 11, of the femur 8 touches the tibia 9 and the medial ligament 10 is stretched to its maximum length $D_m$ for the particular flexion angle. The other parameters of the relative position, in particular the internal/external rotation, the anterior/posterior position and the lateral position are the same as those indicated by the corresponding transformation matrix $T_j$ which is used to determine both the maximum varus and maximum valgus angles.

The maximum varus and/or valgus angles are calculated for each recorded transformation matrix $T_j$. This results in a calculated, predicted post-operative envelope for the range of motion, as shown in the screenshot in FIG. 13 which is from a computer program which is running on the computer 2 and implementing the present invention. If the envelope of the range of motion is satisfactory, then the implants and the implant positions used to predict this range of motion can be implemented in actual arthroplasty, which again is not itself part of the present invention. As can be seen from the screenshot in FIG. 13, the parameters of the implants can be amended in order to predict the range of motion for different sets of parameters.

The relative positions shown in FIGS. 8 and 9 can be calculated in a number of ways. Two examples of possible approaches shall be described in more detail in the following.

In the first approach, the condyles of the femoral implant 8c are modelled as ellipses, as shown in FIGS, 10 and 11. The two ellipses representing the condyles are spaced apart by a distance $d_e$. The sizes of the ellipses and the distance $d_e$ depend on the femoral implant 8c selected.

In this first approach, the two ellipses representing the condyles 8a, 8b are first brought into contact with the surface of the tibia 9. For this purpose, the minimum distances between the two ellipses and the cutting plane P of the tibia (or the surface of the tibia in general) are calculated, as shown in the side view in FIG. 10. These two distances are then used to calculate the angle by which the femur 8, including the implant 8c, has to be rotated and the distance by which the femur 8 and the tibia 9 have to be moved translationally relative to each other in order for the two ellipses to touch the surface of the tibia 9. For this purpose, the axis of rotation and the translational direction have to be known. In one implementation example, they are calculated as follows.

The axis of rotation is defined by a vector $r_{impl}$ which is calculated as $$\vec{r}_{impl} = \vec{n}_{sp} \times (\vec{t}_{cut\_ant} \times \vec{n}_{sp})$$

where $t_{cut\_ant}$ is a vector pointing in the anterior direction of the tibia 9 and lying in the cutting plane P and $n_{sp}$ is a vector pointing to the right-hand side of the femur 8. The vector $n_{sp}$ is calculated as $$\vec{n}_{sp} = \vec{f}_{ant} \times \vec{f}_{mech}$$

where $f_{ant}$ is a vector pointing in the anterior direction of the femur and $f_{mech}$ is a vector corresponding to the mechanical axis of the femur. The vector $r_{impl}$ thus represents the line forming the intersection between the femoral sagittal plane and the tibial cutting plane P.

The vector $$\vec{f}_{up} = \vec{f}_{impl\_right} \times \vec{r}_{impl}$$

is then used together with the vector $$\vec{f}_{impl\_right} = M \cdot \vec{f}_{right}$$

to calculate the angle by which the femoral implant has to be rotated about the line defined by $r_{impl}$ as $$\beta = \cos^{-1}\left(\frac{\vec{f}_{up} \cdot \vec{n}_{tibia\_cut}}{|\vec{f}_{up}||\vec{n}_{tibia\_cut}|}\right).$$

The index i has been omitted from the vectors in order to improve the legibility of the formulae. The vector $f_{impl\_right}$ points to the right-hand side of the femoral implant 8c and is calculated from the vector $f_{right}$ which points to the right-hand side of the femur 8 and the transformation matrix M which represents the position of the femoral implant 8c relative to the femur 8. The vector $n_{tibia\_cut}$ represents the normal vector to the tibia cutting plane P. A rotation matrix $R_i$ can be defined in terms of $\beta_i$ and $r_{impl,i}$ and represents the rotation needed in order to move the femur 8 into a position relative to the tibia 9 in which its condyles 8a and 8b are equally distant from the surface of the tibia 9.

The distance g by which the femur 8 has to be moved translationally relative to the tibia 9 is given by the shortest distance between the ellipse which represents the condyle and the surface of the tibia 9, as shown in FIG. 10. This is a merely two-dimensional problem. The point E on the ellipse which is nearest to the tibia 9 must have a tangent which is parallel to the surface of the tibia 9 (which is modelled as being planar). Reduced to two dimensions, this plane which defines the tibial surface becomes a line. The desired distance g is the distance between this line and the tangent to the ellipse, which is parallel to said line. The tangent can be calculated from the standard equation for an ellipse.

As can be seen from the schematic drawing in RG. 11, the contact point of one ellipse—in this case, the medial ellipse—is fixed and used as the centre of rotation. The lateral ligament 11 and two ellipses representing the femoral implant 8c are indicated in their starting position by continuous lines. In its starting position, the lateral ligament 11 is not fully stretched. The femur 8 is then rotated about its contact point with the tibia 9 such that the opposing ligament—in FIG. 11, the lateral ligament 11—is stretched to its maximum length. The lateral ligament 11 and the two ellipses are indicated in this position by dotted lines. The rotation is indicated by a curved arrow. The rotation moves the feature point $F_l$ upwards and to the left. The angle α, which represents the maximum varus angle, is then calculated using simple trigonometric functions. This process is then repeated, with the other ellipse remaining in contact with the tibia 9 while the femur 8 is rotated until the opposing medial ligament 10 is fully stretched.

Alternatively, the condyles are not modelled as ellipses but are rather represented by the actual shape of the femoral implant, as shown in FIG. 12. In this case, a suitable mathematical description of the implant surface will most likely not be available. Instead of calculating the extent of the relative rotational and translational movement between the femur 8 and the tibia 9, an iterative approach can be applied. The relative position between the femur 8 and the tibia 9 is first altered by a translational movement along, $n_{sp}$ until one of the condyles touches the surface of the tibia 9. The femur 8 is then rotated about the contact point and the vector $r_{impl}$ until the other condyle touches the tibia. This process can be repeated if the first condyle is no longer touching the surface of the tibia after the rotation. Collision detecting techniques are preferably applied in order to detect whether or not a condyle of the femoral implant 8c is in contact with the tibia 9 (or tibial implant 9a).

In a second general approach, the two condyles of the femur 8 are not initially brought into contact with the tibia 9, as in the first approach. Instead, the feature point or $F_m$ or $F_1$ which a ligament connects to the femur 8 is used as the centre of rotation for the femur 8. The position of the point $F_m$ relative to the tibia 9 as shown in FIG. 2 is for example fixed as the centre of rotation, because the post-operative position of the point $F_m$ relative to the tibia 9 is assumed to be equal to the pre-operative relative position. The femur is then rotated about this point, about the vector $r_{impl}$ which is calculated as in the first approach, until the opposite condyle is in contact with the tibia 9. Thus, if the point $F_m$ is for example fixed as the centre of rotation, then the femur 8 is rotated about this point until the lateral condyle 8h touches the tibia 9. Whether or not the femur and the tibia are touching can be determined using known collision detecting techniques.

It should again be noted that the present invention does not comprise any surgical steps but rather merely relates to simulating the predicted outcome of an arthroplasty performed using the assumed parameters for the implant(s).

The invention claimed is:

1. A method for simulating the predicted outcome of an arthoplasty using a medical navigation system, comprising:
   for each of a plurality of flexion angles of a patient's knee joint:
      applying a varus stress to a patient's knee joint;
      measuring, by the medical navigation system, the relative position of the patient's tibia and the patient's femur while applying the varus stress; and
      determining a lateral ligament length of the patient's knee joint;
   for each of a plurality of flexion angles of the patient's knee joint:
      applying a valgus stress to the patient's knee joint;
      measuring, by the medical navigation system, the relative position of the patient's tibia and the patient's femur while applying the valgus stress; and
      determining the medial ligament length of the patient's knee joint;

based at least on the determined patient's medial ligament length and the determined patient's lateral ligament length and for each of the plurality of flexion angles,
determining, by a computer of the medical navigation system, for each of a femoral implant and a tibial implant, a maximum valgus angle; and a maximum varus angle;
determining, by the computer of the medical navigation system, a range of motion envelope over the plurality of flexion angles containing the maximum valgus angle and the maximum varus angle at the respective flexion angle for the femoral implant and the tibial implant;
displaying the range of motion envelope for the femoral implant and the tibial implant;
receiving input to amend at least one position or size parameter for at least one of the tibial implant or the femoral implant based on the displayed range of motion envelope; and
displaying a modified range of motion envelope based upon the received input.

2. The method of claim 1 wherein the determining the medial ligament length and determining the lateral ligament length of the patient's knee joint is accompanied by attaching a first marker to the patient's tibia and attaching a second marker to the patient's femur.

3. The method of claim 1 wherein the determining the medial ligament length and determining the lateral ligament length of the patient's knee joint includes forming a transformation matrix which represents the relative position between the tibia and the femur in which the lateral ligament of the patient or the medial ligament of the patient is stretched to its maximum length.

4. The method of claim 1 wherein the determining the medial ligament length and determining the lateral ligament length of the patient's knee joint is accomplished by creating a surface model of the femur.

5. The method of claim 4 wherein the determining the medial ligament length and determining the lateral ligament length of the patient's knee joint is accomplished by creating a surface model of the tibia.

6. The method of claim 1 wherein the determining the medial ligament length and determining the lateral ligament length of the patient's knee joint includes forming a transformation matrix.

7. The method of claim 1 wherein the determining by the computer of the medical navigation system, the range of motion envelope is further based on the femoral implant particular position and the tibial implant particular position.

8. The method of claim 1 further comprising:
defining a tibial cutting plane;
wherein the medial ligament length and the lateral ligament length of the patient are determined in relation to the formed tibial cutting plane.

9. The method of claim 8 wherein the defined tibial cutting plane is a virtual tibial plane.

10. The method of claim 8 wherein the tibial cutting plane is formed by cutting an upper end of the patient's tibia and the length of the lateral ligament and the length of the medial ligament is measured perpendicular to the tibial cutting plane.

11. The method of claim 1 wherein displaying the range of motion envelope further includes describing the range of motion over the plurality of flexion angles along an axis.

12. The method of claim 11 wherein displaying of the range of motion envelope over the plurality of flexion angles includes:
presenting the maximum valgus angle and the maximum varus angle for each particular flexion angle along the axis.

13. A method for simulating the predicted outcome of an arthoplasty using a medical navigation system, comprising:
forming a tibial plane with the medical navigation system and markers;
determining, by a computer of the medical navigation system, a transformation matrix which represents a relative position between the patient's femur and the tibia;
determining a maximum length of a lateral ligament of the patient and a maximum length of a medial ligament of the patient based upon the transformation matrix and in relation to the tibial plane over a plurality of flexion angles;
based at least on the determined length of the lateral ligament and determined length of the medial ligament and for each of at least one of a femoral implant or a tibial implant and for each of a plurality of flexion angles,
determining by the computer of a medical navigation system: a maximum valgus angle; and a maximum varus angle;
determining a range of motion envelope over the plurality of flexion angles, the range of motion envelope containing the maximum valgus angle and the maximum varus angle at the respective flexion angle for the at least one of the femoral implant or tibial implant; and
displaying the range of motion envelope for the at least one of the determined range of motion for the at least one of the femoral implant or the tibial implant over the plurality of flexion angles.

14. The method of claim 13 further including:
receiving input to amend at least one position or size parameter for the at least one of the tibial implant or the femoral implant based on the displayed range of motion envelope; and
displaying on a modified range of motion envelope based upon the received input.

15. The method of claim 13 wherein displaying the range of motion envelope further includes describing the range of motion over the plurality of flexion angles along an axis.

16. The method of claim 13 wherein the forming the tibial plane is a virtual tibial plane.

17. The method of claim 13 wherein the tibial plane is formed by cutting an upper end of the patient's tibia and the length of the lateral ligament and the length of the medial ligament is measured perpendicular to the tibial plane.

18. A method for simulating the predicted outcome of an arthoplasty using a medical navigation system, comprising:
forming a tibial plane of a patient's tibia with the medical navigation system and markers;
measuring by the medical navigation system a relative position between a patient's femur and the patient's tibia;
determining based upon the measured relative position a maximum length of the patient's lateral ligament and a maximum length of the patient's medial ligament over a plurality of flexion angles, wherein the maximum length of the lateral ligament and the maximum length of the medial ligament is determined in relation to the formed tibial plane;
based at least on the determined length of the lateral ligament and medial ligament and for at least one of a femoral implant or tibial implant and for each of a plurality of flexion angles, determining by a computer of the medical navigation system:
   a maximum valgus angle; and
   a maximum varus angle;
determining a range of motion envelope over the plurality of flexion angles, the range of motion envelope containing the maximum valgus angle and the maximum varus angle at the respective flexion angle for the at least one femoral implant or tibial implant;
wherein the determining the range of motion envelope is further based on at least one of a femoral implant position relative to the femur of the patient or a tibial implant position relative to the tibia of the patient; and
displaying the range of motion envelope for the determined range of motion for the at least one of the femoral implant or the tibial implant over the plurality of flexion angles.

\* \* \* \* \*

UNITED STATES PATENT AND TRADEMARK OFFICE
CERTIFICATE OF CORRECTION

| | |
|---|---|
| PATENT NO. | : 10,813,574 B2 |
| APPLICATION NO. | : 15/794754 |
| DATED | : October 27, 2020 |
| INVENTOR(S) | : Fleig et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 541 days.

Signed and Sealed this
Fourteenth Day of February, 2023

*Katherine Kelly Vidal*

Katherine Kelly Vidal
*Director of the United States Patent and Trademark Office*